(12) United States Patent
Asano

(10) Patent No.: US 6,249,697 B1
(45) Date of Patent: Jun. 19, 2001

(54) ELECTROGASTROGRAPH AND METHOD FOR ANALYZING DATA OBTAINED BY THE ELECTROGASTROGRAPH

(75) Inventor: Fumitaka Asano, Saitama (JP)

(73) Assignees: Nipro Corporation, Osaka; Gram Corporation, Shizuoka, both of (JP)

( * ) Notice: Subject to any disclaimer, the term of this patent is extended or adjusted under 35 U.S.C. 154(b) by 0 days.

(21) Appl. No.: 09/329,788

(22) Filed: Jun. 10, 1999

(30) Foreign Application Priority Data

Jun. 15, 1998 (JP) .................................................. 10-183373

(51) Int. Cl.⁷ ................................................ A61B 5/0488
(52) U.S. Cl. .............................................................. 600/546
(58) Field of Search ..................... 600/546, 593; 607/40

(56) References Cited

U.S. PATENT DOCUMENTS 5,795,304 * 8/1998 Sun et al. .............................. 600/546
5,995,872 * 11/1999 Bourgeois .............................. 607/40

* cited by examiner

*Primary Examiner*—Jeffrey R. Jastrzab
(74) *Attorney, Agent, or Firm*—Browdy & Neimark

(57) ABSTRACT

An electrogastrograph measures an electric signal derived from the stomach's action. The signal is decomposed into its frequency components by means of a plurality of band pass filters, and stored in a storage medium. A method for analyzing data obtained by the electrogastrograph comprises the steps of: decomposing the signal into its frequency components by means of the band pass filters; and, evaluating the stomach in its action on the basis of variations in amplitude of said frequency components.

13 Claims, 3 Drawing Sheets

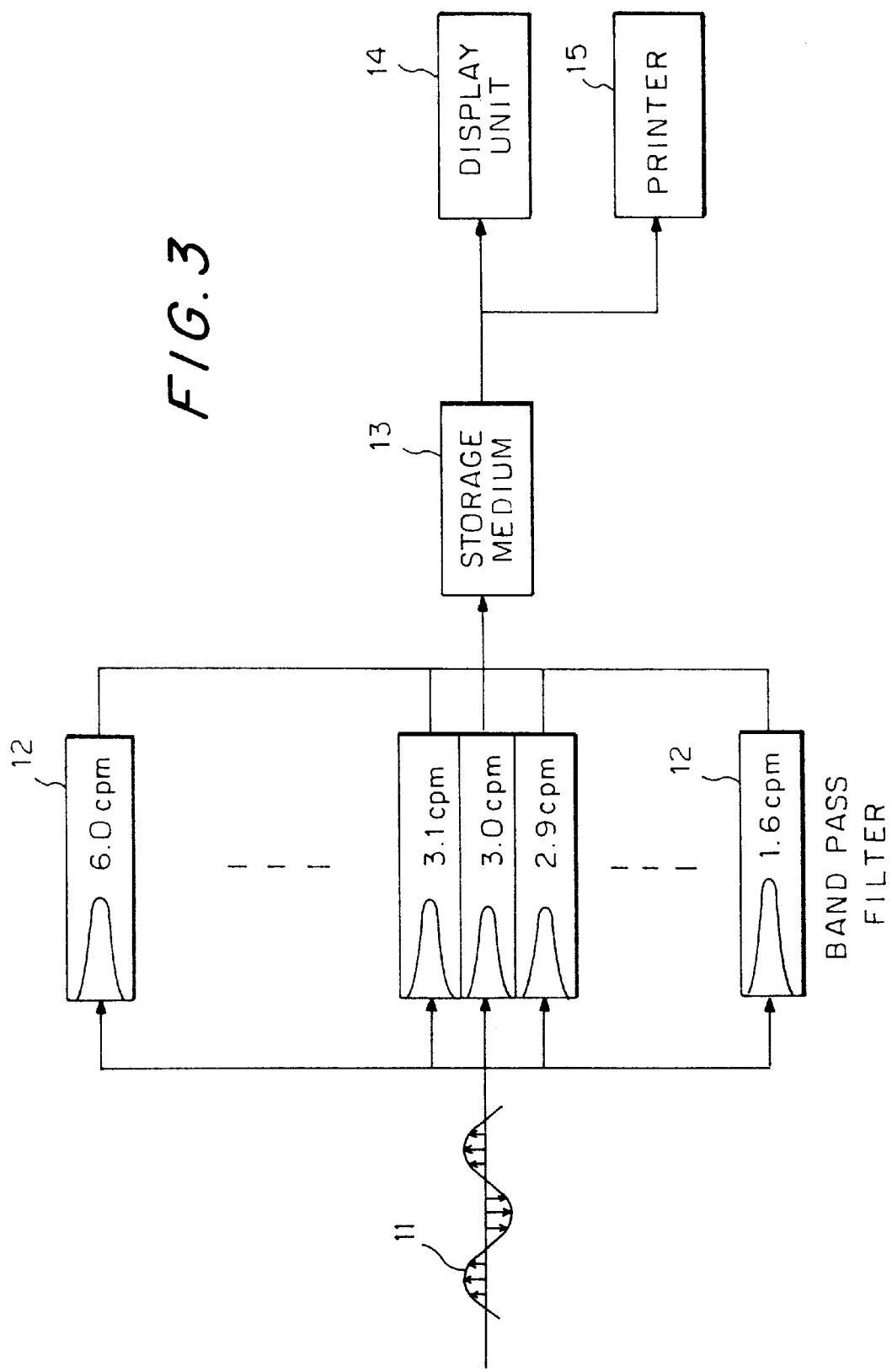

ELECTROGASTROGRAPH AND METHOD FOR ANALYZING DATA OBTAINED BY THE ELECTROGASTROGRAPH

BACKGROUND OF THE INVENTION

1. Field of the Invention

The present invention relates to an electrogastrograph and a method for analyzing data obtained by the electrogastrograph, wherein the electrogastrograph is an apparatus for measuring an electric signal (hereinafter referred to as the stomach signal) produced in the stomach when the stomach goes into action.

2. Description of the Related Art

Heretofore, it has been known to use a method for measuring such stomach signal derived from the stomach's action, in which method, only frequency bands containing the stomach signal are obtained through combination of low-pass filters with high-pass filters, wherein the low-pass filters are used to remove essentially breath signals, and the high-pass filters are used to remove essentially the influence of the body action, so that only the frequency bands containing the stomach signal thus obtained are recorded in a suitable storage medium. In this case, the stomach's action produces 9 slow wave signal that occurs approximately three times a minute, and is very small in variation in its cycle. Consequently, in order to find out or extract the cycle of the stomach signal thus measured, peak frequencies resulted from the Fourier transform such as FFT and like transforms of the thus measured stomach signal are used.

Now, problems to be solved by the present invention will be described.

In general, in order to evaluate the stomach's action, 0.1 cpm (i.e., cycle/minute) resolution is required. In order to achieve this resolution, it is necessary for the conventional Fourier transform to use the amount of data obtained over a period of 10 minutes. Furthermore, the thus obtained result shows an average value of the data obtained over the period of 10 minutes. However, in general, the stomach's action varies drastically in two or three minutes. Consequently, it is not possible for the conventional Fourier transform to process such drastic variations in the stomach's action.

The stomach signal taken out of an electrode attached to a human body surface is feeble, and, therefore always suffers from a relatively high level noise even when the high-pass filters are used to remove the influence which the body action exercises on the stomach signal. When the stomach signal mixed with such noise is subjected to the Fourier transform, its noise components become dominant over all the others to hidden the stomach signal therein, which means that it is impossible to analyze the stomach signal over an extended period of time, for example such as twenty minutes in total before and after noise mixture occurs. However, in a real life, it is substantially impossible to prevent such a noise derived from the body action from entering the stomach signal over such an extended period of time, for example, over twenty minutes in total. Consequently, in the conventional method, it is substantially impossible to analyze the stomach signal occurring in the real life.

SUMMARY OF THE INVENTION

Under such circumstances, the present invention was made to solve the problems inherent in the related art described above. Consequently, it is an object of the present invention to provide an electrogastrograph and a method for analyzing data obtained by this electrogastrograph, wherein the electrogastrograph of the present invention is capable of: catching the stomach's action which varies drastically in a brief space of time, for example, in two or three minutes; and, clearly identifying the body action, which enables a user of the electrogastrograph of the present invention to analyze the stomach signal in daily life without fail, wherein the stomach signal is an electric signal derived from the stomach's action in daily life.

According to a first aspect of the present invention, the above object of the present invention is accomplished by providing:

An electrogastrograph which is an apparatus for measuring an electric signal derived from the stomach's action, the electrogastrograph being characterized in that:

the electric signal derived from the stomach's action is decomposed into its frequency components by means of a series of filters constructed of a plurality of band pass filters.

In the electrogastrograph as set forth in the first aspect of the present invention, preferably, the electric signal having been decomposed into the frequency components thereof is capable of being stored in a suitable storage medium.

According to a second aspect of the present invention, the above object of the present invention is accomplished by providing:

A method for analyzing data obtained by an electrogastrograph, comprising the steps of:

decomposing an electric signal into its frequency components by means of a series of filters constructed of a plurality of band pass filters, the electric signal having been derived from the stomach's action and measured; and, evaluating the stomach in its action on the basis of variations in amplitude of the frequency components.

Namely, in the present invention having the above construction, there are provided a plurality of band pass filters the number of which is equal to the number of frequency bands being analyzed, wherein the band pass filters have their cut-off frequencies staggered on their passing band widths, so that the stomach signal is: directly; or, after removal of the influences of the body action and the breath action, i.e., indirectly; analyzed by these band pass filters into the individual frequency components of the stomach signal. More specifically, a signal extracted by one of the band pass filters produces an amplitude proportional to the magnitude of the frequency component extracted by the band pass filter. This amplitude is analogous to the amplitude of the frequency component in the Fourier transform.

Resolution in time of the band pass filter is largely depending on the delay properties of the filter. In this connection, as for the band pass filer having a passing band width of 0.1 cpm, it is possible to obtain approximately 1 minute of resolution, which makes it possible to catch, without fail, the stomach's action varying on a minute-to-minute basis.

Further, since the response time of the band pass filter is on a minute-to-minute basis, the influence of the noise caused by the body action goes out in one or two minutes. Further, since the noise contains a wide range of frequency components, it is possible to clearly distinguish the stomach signal from the noise through spectrum analysis of amplitude.

BRIEF DESCRIPTION OF THE DRAWINGS

FIG. 3 is a block diagram illustrating the flow of procedures when the method of the present invention for analyzing the data is carried out by the computer, wherein the data is obtained by the electrogastrograph of the present invention.

DETAILED DESCRIPTION OF THE PREFERRED EMBODIMENTS

Now, with reference to the accompanying drawings, the present invention will be described in detail using its preferred embodiments.

Incidentally, a filters used in the present invention may be of an analog type or of a digital type. In the present invention, since a large number of filters are required, the filters are preferably of the digital type. The following description will be made on the case that the filters are of digital type.

Figure 1:
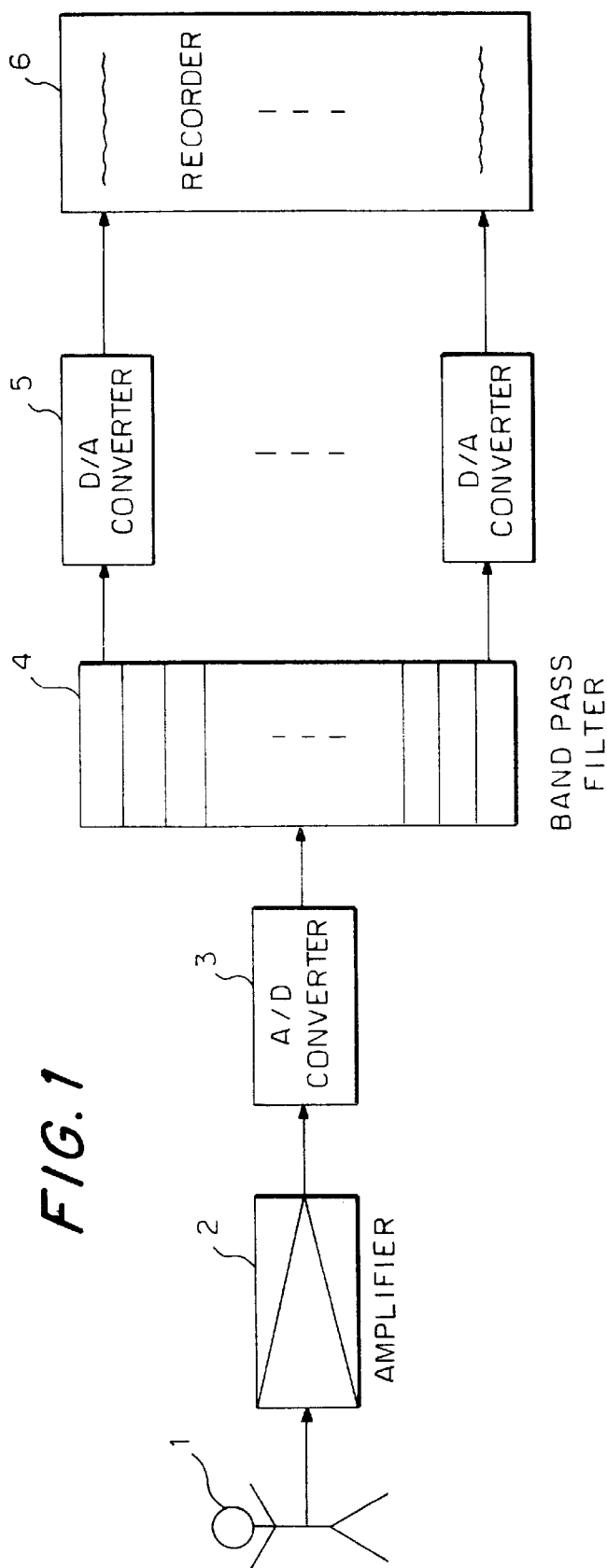
FIG. 1 is a block diagram of an embodiment of the electrogastrograph of the present invention.
Figure 2:
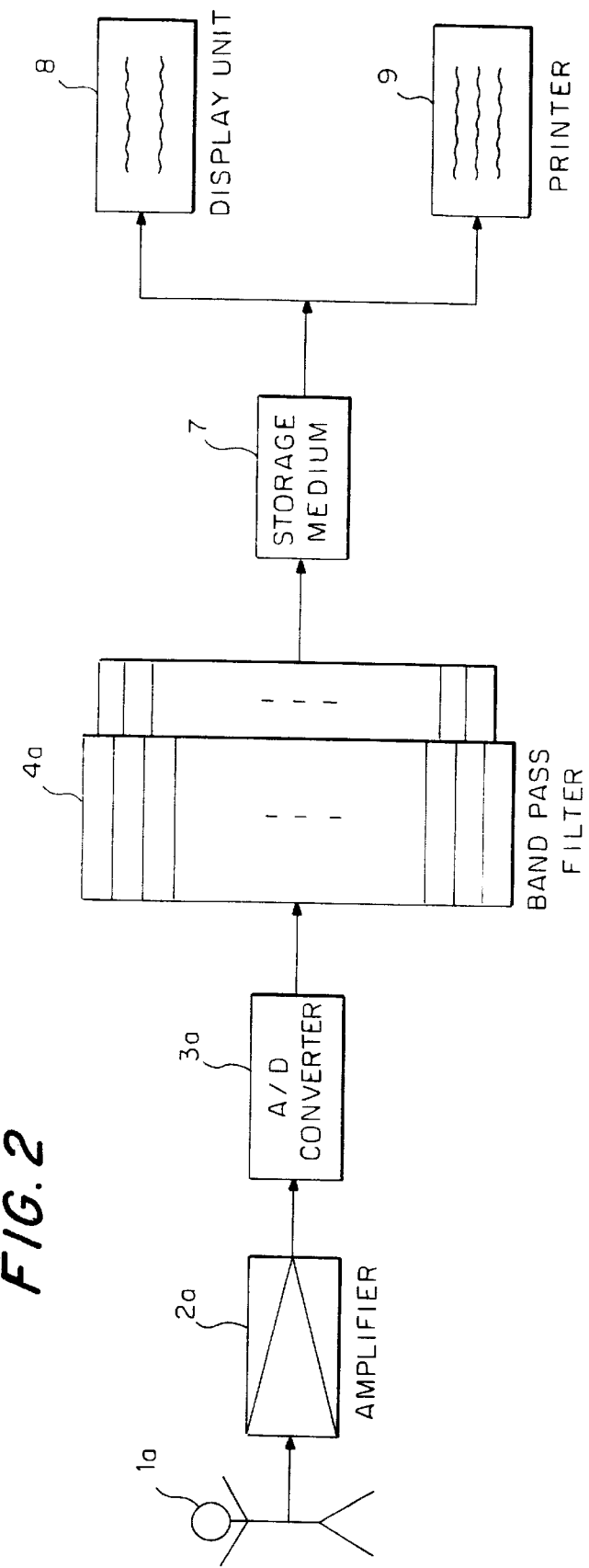
FIG. 2 is a block diagram of another embodiment of the electrogastrograph of the present invention.

As shown in FIGS. 1 and 2, the stomach signal is taken out of an electrode attached to a human body 1, 1a, amplified by an amplifier 2, 2a to reach a suitable amplitude level, and then converted by an A/D converter 3, 3a into a digital signal. The thus converted digital signal is then inputted to a series of filters 4, 4a constructed of a plurality of band pass filters in which a digital operation (hereinafter referred to as the filter operation) is performed to issue an electric signal representing the result of the filter operation performed in the filters (which electric signal is hereinafter referred to as the filter operation result signal). In FIG. 1, this filter operation result signal is issued to a D/A converter 5 in which the filter operation result signal is converted into an analog signal. This analog signal thus converted in the D/A converter is then recorded in a multi-channel recorder 6. In the above construction, it is also possible to replace both the D/A converter 5 and the multi-channel recorder 6 with a suitable printer. In this case, it is possible to issue the filter operation result signal to the printer.

Another embodiment of the present invention is shown in FIG. 2, in which: the filter operation result signal produced in the series of the filters 4a is recorded in a suitable storage medium 7. The filter operation result signal produced in the series of the filters 4a is recorded in the storage medium 7, and can be immediately outputted to a display unit 8 and/or a printer 9. However, in general, after completion of measurement, data stored in the storage medium 7 is transferred to another computer for further analysis.

FIG. 3 shows a method for processing the stomach signal by using the filters in the computer. The stomach signal 11 shown in FIG. 3 may be of the data obtained from an A/D converter incorporated in a computer, or may be of the data obtained from the storage medium 7. This stomach signal 11 is inputted to the individual band pass filters 12 of a series of filters, so that operations in these filters are performed, whereby a filter operation result signal is issued from the band pass filters 12 to a suitable storage medium 13 and recorded therein. It is also possible for the storage medium 13 to further transfer the filter operation result signal to a display unit 14 and/or a printer 15 for printing out the data.

As described above, the filter operation result signals thus obtained are directly displayed as a graph expressed in color scale for showing in amplitude the signal components thus extracted in the individual filters. Based on the thus displayed graph, it is possible to judge the stomach's action in variation and in mode change. Incidentally, the series of the filters shown in FIG. 3 is constructed of 44 pieces of the band pass filters each with resolution of 0.1 cpm to cover a resolution range of from 1.6 to 6.0 cpm.

The following is a concrete example of operations performed in the band pass filters, in which a fourth order Butterworth filter is constructed of a plurality of digital filters of cascade type ID, where: a sampling cycle of the A/D converter is 1 second; an intermediate frequency is 3.0 cpm; and, a passing band width is 0.1 cpm:

*Filter Constant
num[0]=1.0, num[1]=0.0, num[2]=−1.0,
num[3]=1.0, num[4]=0.0, num[5]=−1.0;
den[0]=1.0, den[1]=−1.88897243, den[2]=0.98955152, den[3]=1.0, den[4]=−1.89563999, den[5]=0.98987718;
scale=0.000052898859;
*Operations
sum=data×scale;
for (i=0; i<2; i++){
aw=num[i×3+1]×delay[2×i]+num[i×3+2]×delay[2×i+1];
bw=den[i×3+1]×delay[2×i]+den[i×3+2]×delay[2×i +1];
wo=sum−bw;
sum=wo×num[i×3]+aw;
delay [2×i+1]=delay[2×i];
delay[2×i]=wo; }
a value of the stomach signal is inputted to "data", and the result is outputted to "sum".

The effect of the present invention is as follows: namely, as described above, on the basis of the stomach signal,it is possible for the present invention to precisely catch the stomach's action which considerably varies in a brief space of time. Further, in the present invention having the above construction, it is also possible to clearly distinguish the stomach signal from the body action. Consequently, the present invention has the effect of making it possible to analyze the stomach signal in daily life.

What is claimed is:

1. In a slow wave electrogastrograph for measuring an electric signal derived from the action of the stomach of a subject, the improvement comprising:

a filter system composed of a plurality of band pass filters for decomposing the slow wave electric signal derived from the stomach's action into frequency components of the electric signal.

2. The electrogastrograph as set forth in claim 1, further comprising:

a storage medium connected for storing the electric signal frequency components.

3. The electrogastrograph as set forth in claim 1 wherein each of said filters has a respectively different pass band.

4. The electrogastrograph as set forth in claim 3 wherein each of said filters has a pass band bandwidth of the order of 0.1 cpm.

5. The electrogastrograph as set forth in claim 3 wherein at least two of said filters have pass bands within a range between 1.6 and 6.0 cpm.

6. A slow wave electrogastrograph for measuring an electric signal derived from the action of the stomach of a subject, comprising:

a sensing device for obtaining a slow wave electric signal representative of the action of the stomach of a subject;

a filter system composed of a plurality of band pass filters connected to said sensing device for receiving the electric signal and decomposing the slow wave electric signal into frequency components of the electric signal; and an output device coupled to said filters for providing an output representing a parameter of the frequency components.

7. The electrogastrograph as set forth in claim 6 wherein each of said filters has a respectively different pass band.

8. The electrogastrograph as set forth in claim 7 wherein each of said filters has a pass band bandwidth of the order of 0.1 cpm.

9. The electrogastrograph as set forth in claim 7 wherein at least two of said filters have pass bands within a range between 1.6 and 6.0 cpm.

10. A method for analyzing data obtained by an electrogastrograph, comprising the steps of:

decomposing a slow wave electric signal derived from the action of the stomach of a subject into its frequency components by means of a plurality of band pass filters; and, evaluating the action of the stomach on the basis of variations in amplitude of the frequency components.

11. The method as set forth in claim 10 wherein each of the filters has a respectively different pass band.

12. The method as set forth in claim 11 wherein each of the filters has a pass band bandwidth of the order of 0.1 cpm.

13. The method as set forth in claim 11 wherein at least two of the filters have pass bands within a range between 1.6 and 6.0 cpm.

* * * * *